(12) United States Patent
Ma et al.

(10) Patent No.: US 8,436,154 B2
(45) Date of Patent: May 7, 2013

(54) CRYSTALLIZING METHOD OF ERYTHROMYCIN

(75) Inventors: Xiaoping Ma, Dongguan (CN); Luning Song, Dongguan (CN)

(73) Assignee: Sunshine Lake Pharma Co., Ltd., Northern Industrial Area, Songshan Lake, Dongguan, Guangdong (CN)

( * ) Notice: Subject to any disclaimer, the term of this patent is extended or adjusted under 35 U.S.C. 154(b) by 206 days.

(21) Appl. No.: 13/063,933

(22) PCT Filed: Oct. 29, 2009

(86) PCT No.: PCT/CN2009/001204
§ 371 (c)(1),
(2), (4) Date: Mar. 14, 2011

(87) PCT Pub. No.: WO2010/048786
PCT Pub. Date: May 6, 2010

(65) Prior Publication Data
US 2011/0172402 A1    Jul. 14, 2011

(30) Foreign Application Priority Data
Oct. 29, 2008 (CN) .......................... 2008 1 0225310

(51) Int. Cl.
*C07H 17/08* (2006.01)
(52) U.S. Cl.
USPC ......................................................... 536/7.2
(58) Field of Classification Search .................. 536/7.2
See application file for complete search history.

(56) References Cited

U.S. PATENT DOCUMENTS
2,864,817 A  *  12/1958  Croley ........................... 536/7.5

FOREIGN PATENT DOCUMENTS
| CN | 1513864 A | | 7/2004 |
| RO | 99792 A | * | 6/1990 |
| RO | 99792 A | | 6/1990 |

OTHER PUBLICATIONS

ISR&WO, Feb. 4, 2010.
Eng. translation of ISR.
Comp. translation of B3.
Eng. Abstract of B4.

* cited by examiner

*Primary Examiner* — Shaojia Anna Jiang
*Assistant Examiner* — Ganapathy Krishnan
(74) *Attorney, Agent, or Firm* — Kam W. Law; Squire Sanders

(57) ABSTRACT

The present invention provides an erythromycin crystallizing method, which comprises using dichloromethane containing solvent as a preparation solvent, and the dichloromethane solution of erythromycin received was gradiently cooled from high temperature down to low temperature, and thus making erythromycin crystallize. According to the method of the present invention, the content of erythromycin A is high, the content of erythromycin A in the erythromycin crystalline is more than 94.5% (HPLC detection method), the content of dichloromethane in the erythromycin crystalline is less than 600 ppm, the content of water in the erythromycin crystalline is less than 2.5%, the microbiological titre of the erythromycin crystalline is more than 940 μ/mg.

10 Claims, No Drawings

CRYSTALLIZING METHOD OF ERYTHROMYCIN

This is a U.S. national stage application of the International Patent Application No. PCT/CN2009/001204, filed Oct. 29, 2009, which claims priority to Chinese Patent Application No. 200810225310.8, filed Oct. 29, 2008, both of which are incorporated herein by reference in their entirety.

FIELD OF THE INVENTION

The present invention relates to a method for recrystallizing erythromycin.

BACKGROUND OF THE INVENTION

Erythromycin, $C_{37}H_{67}NO_{13}$, molecular weight of 733.94, is an antibiotic having a 14-membered macrolide ring. It has an antimicrobial spectrum similar to or slightly wider than that of penicillin and has a strong antibacterial effect against the G+ bacteria. It can be used as a raw material for preparing erythromycin-containing material or a starting material for preparing erythromycin derivatives.

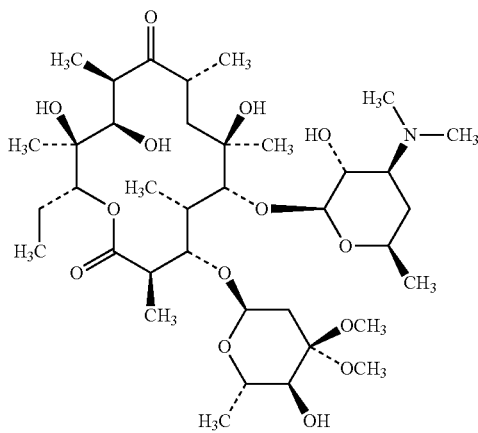

CN1513864A discloses a dynamic recrystallization method for preparing erythromycin from an erythromycin salt, which uses acetone and water as solvents. The amount of erythromycin A in the product formed is less than 93%. The amount of water in erythromycin crystals is more than 3.5%. The microbiological titre of the erythromycin crystals is less than 930 μ/mg.

This invention uses a new solvent to obtain erythromycin having a better quality. The amount of erythromycin A in the erythromycin crystals (HPLC detection method) is more than 94.5%. The amount of dichloromethane in the erythromycin crystals is less than 600 ppm. The amount of water in the erythromycin crystals is less than 2.5%. The microbiological titre of the erythromycin crystals is more than 940 μ/mg.

DESCRIPTIONS OF THE INVENTION

The purpose of the present invention is to provide a method for recrystallizing erythromycin which is able to form a product with a higher amount of erythromycin A.

To achieve the purpose of the present invention, the method for recrystallizing erythromycin of this invention comprising the steps:

1) first dissolving erythromycin or an erythromycin salt in dichloromethane or a solvent mixture comprising dichloromethane under alkaline condition to form an erythromycin solution;
2) then cooling the erythromycin solution gradiently from 37° C. to −5° C. to form a suspension of erythromycin crystals;
3) then separating the erythromycin crystals from the suspension;
4) and finally washing and drying the crystals.

wherein the erythromycin salt can be erythromycin thiocyanate or erythromycin lactate.

The solvent mixture comprising dichloromethane can further comprise any one of ethanol, acetone, ethyl acetate or butyl acetate or other similar alcohols, ketones or esters. The volume content of dichloromethane in the solvent mixture is from 60 to 100%.

The alkaline condition refers to the pH of the erythromycin solution is 8.6-12.

The amount of erythromycin A in the erythromycin solution is from 4 to 20%, preferably from 14 to 16%.

The temperature is gradiently cooled from 37° C. to −5° C. at a cooling rate of 1 to 10° C. per hour for a recrystallization time period from 2 to 36 hours. Preferably, the temperature of the erythromycin solution is kept at 23-28° C. for 1 to 10 hours during the gradiently cooling.

The separating step can be done by commonly used equipment in the field, such as centrifuges, filtration equipment and so on.

The erythromycin crystals separated by centrifugation can be washed by an organic solvent or pure water and the residue of the solvent in the erythromycin crystals can be removed by a drying method.

The organic solvent comprises more than 90% of dichloromethane, and other organic solvent components such as alcohols, ketones or esters.

By testing, the amount of erythromycin A in the erythromycin crystals (HPLC detection method) is more than 94.5%. The amount of dichloromethane in the erythromycin crystals is less than 600 ppm. The amount of water in the erythromycin crystals is less than 2.5%. The microbiological titre of the erythromycin crystals is more than 940 μ/mg.

This invention utilizes the fact that the solubility of erythromycin in the solvent comprising dichloromethane decreases with a decrease in temperature. The erythromycin dissolved in the dichloromethane solvent is gradiently cooled from a high temperature to a low temperature to form the erythromycin crystals and to form a product with a higher amount of erythromycin A.

EXAMPLES

The experimental examples are only intended to be illustrative of the present invention but not to be used to limit the scope of the present invention.

Example 1

Erythromycin thiocyanate (200 g) was added into dichloromethane (500 mL), stirred under heat to 37° C. and adjusted to pH 12 until the solution became clear. The upper aqueous phase was separated and removed to obtain a dichloromethane solution with about 14% of erythromycin A. The dichloromethane solution was cooled to 24° C., kept for 2 hours and then cooled to −4° C. in 5 hours. The crystals formed were filtered. Dichloromethane (20 mL) was used to wash the crystals and the crystals were filtered for further 5 minutes. The amount of the erythromycin A in the dried erythromycin is 95.2% with a dichloromethane content of 150 ppm, a water content of 1.0% and a microbiological titre of 948 μ/mg.

Example 2

Erythromycin (100 g) was added into dichloromethane (600 mL), stirred under heat to 35° C. and adjusted to pH 10 until the solution became clear. The upper aqueous phase was separated and removed to obtain a dichloromethane solution with about 16% of erythromycin A. The dichloromethane solution was cooled to 28° C., kept for 5 hours and then cooled to −2° C. in 5 hours. The crystals formed were filtered. Dichloromethane (20 mL) was used to wash the crystals and the crystals were filtered for further 5 minutes. The amount of erythromycin A in the dried erythromycin is 96.0% with a dichloromethane content of 178 ppm, a water content of 0.9% and a microbiological titre of 955 μ/mg.

Example 3

A mixture of erythromycin thiocyanate and other impurities (100 g) was added into a solvent mixture (300 mL) comprising dichloromethane and acetone (the volume content of dichloromethane is 60%), stirred under heat to 34° C. and adjusted to pH 12 until the solution became clear. The upper aqueous phase was separated and removed to obtain a dichloromethane solution with about 15% of erythromycin A. The dichloromethane solution was cooled to 23° C., kept for one hour and then cooled to 3° C. in 16 hours. The crystals formed were filtered. Dichloromethane (20 mL) (the content of dichloromethane is 95% and ethanol is 5%) was used to wash the crystals and the crystals were filtered for further 5 minutes. The amount of erythromycin A in the dried erythromycin is 94.6% with a dichloromethane content of 352 ppm, a water content of 2.2% and a microbiological titre of 941 μ/mg.

Example 4

Erythromycin (100 g) was added into dichloromethane (600 mL). Acetone (20 mL) was added, stirred under heat to 35° C. and adjusted to pH 9.8 until the solution became clear. The upper aqueous phase was separated and removed to obtain a dichloromethane solution with about 15% of erythromycin A. The dichloromethane solution was cooled to 24° C., kept for 2 hours and then cooled to 0° C. in 8 hours. The crystals formed were filtered. Dichloromethane (20 mL) was used to wash the crystals and the crystals were filtered for further 5 minutes. The amount of erythromycin A in the dried erythromycin is 95.4% with a dichloromethane content of 247 ppm, a water content of 1.2% and a microbiological titre of 946 μ/mg.

Example 5

A mixture of erythromycin thiocyanate and other impurities (100 g) was added into dichloromethane (300 mL). Butyl acetate (or ethyl acetate) (50 mL) was added, stirred under heat to 34° C. and adjusted to pH 12 until the solution became clear. The upper aqueous phase was separated and removed to obtain a dichloromethane solution with about 15% of erythromycin A. The dichloromethane solution was cooled to 23° C., kept for 2 hours and then cooled to −5° C. in 16 hours. The crystals formed were filtered. Dichloromethane (20 mL) was used to wash the crystals and the crystals were filtered for further 5 minutes. The amount of erythromycin A in the dried erythromycin is 94.8% with a dichloromethane content of 385 ppm, a water content of 1.1% and a microbiological titre of 943 μ/mg.

Example 6

A mixture comprising erythromycin (100 g) was added into dichloromethane (600 mL). Ethanol (30 mL) was added, stirred under heat to 35° C. and adjusted to pH 8.6 until the solution became clear. The upper aqueous phase was separated and removed to obtain a dichloromethane solution with about 15% of erythromycin A. The dichloromethane solution was cooled to 23° C., kept for 2 hours and then cooled to 0° C. in 12 hours. The crystals formed were filtered. Dichloromethane (20 mL) (the content of dichloromethane is 95% and ethanol is 5%) was used to wash the crystals and the crystals were filtered for further 5 minutes. The amount of erythromycin A in the dried erythromycin is 96.0% with a dichloromethane content of 180 ppm, a water content of 1.2% and a microbiological titre of 944 g/mg.

INDUSTRIAL APPLICABILITY

The method for recrystallizing erythromycin of this invention, which comprises using dichloromethane-containing solvent as a preparation solvent, and cooling the erythromycin-containing dichloromethane solution gradiently from a high temperature to a low temperature, and thus forming erythromycin crystals. The amount of the erythromycin A in the erythromycin crystals (HPLC detection method) is more than 94.5%, with the content of dichloromethane less than 600 ppm, the amount of water less than 2.5%, and the microbiological titre more than 940 μ/mg. A higher amount of erythromycin A can be formed by the method of recrystallization of erythromycin of the present invention, therefore it capable of industrial application.

The invention claimed is:
1. A method for recrystallizing erythromycin, comprising the steps:
  (1) first dissolving erythromycin or an erythromycin salt in dichloromethane or a solvent mixture comprising dichloromethane under alkaline condition to form an erythromycin solution, wherein the pH of the erythromycin solution is from 8.6 to 12;
  (2) then cooling the erythromycin solution gradiently from 37° C. to −5° C. to form a suspension of erythromycin crystals, wherein a temperature is gradiently cooled from 37° C. to −5° C. at a cooling rate of 1° C. to 10° C. per hour for a recrystallization time period from 2 hours to 36 hours;
  (3) then separating the erythromycin crystals from the suspension; and
  (4) finally washing and drying the crystals.
2. The method of claim 1, wherein the solvent mixture comprising dichloromethane further comprises a solvent selected from the group consisting of ethanol, acetone, ethyl acetate and butyl acetate; and the volume content of dichloromethane in the solvent mixture is from 60 to 100%.
3. The method of claim 1, wherein the amount of erythromycin A in the erythromycin solution is from 4 to 20%.
4. The method of claim 1, wherein the temperature of the erythromycin solution is kept at 23-28° C. for 1 to 10 hours during the gradient cooling.
5. The method of claim 1, wherein an organic solvent or pure water is used for washing.

6. The method of claim 5, wherein the organic solvent comprises more than 90% of dichloromethane and another organic solvent component, wherein the organic solvent component is an alcohol, ketone or ester.

7. The method of claim 2, wherein the amount of erythromycin A in the erythromycin solution is from 4% to 20%.

8. The method of claim 2, wherein an organic solvent or pure water is used for washing.

9. The method of claim 3, wherein an organic solvent or pure water is used for washing.

10. The method of claim 4, wherein an organic solvent or pure water is used for washing.

* * * * *